United States Patent [19]

Buchanan

[11] Patent Number: 4,836,780

[45] Date of Patent: Jun. 6, 1989

[54] ANTI-CURVATURE DENTAL ROOT CANAL SHAPING FILE

[76] Inventor: L. Stephen Buchanan, 179 Hermosillo Rd., Montecito, Calif. 93108

[21] Appl. No.: 899,419

[22] Filed: Aug. 22, 1986

[51] Int. Cl.[4] .............................................. A61C 5/02
[52] U.S. Cl. ..................................... 433/102; 433/72; 433/75
[58] Field of Search .................... 433/102, 81, 224, 72

[56] References Cited

U.S. PATENT DOCUMENTS

| | | | |
|---|---|---|---|
| D. 250,544 | 12/1978 | Leonard | D24/10 |
| 251,598 | 12/1881 | Johanson | 433/102 |
| 3,908,270 | 9/1975 | Fishman | 433/224 |
| 3,949,479 | 4/1976 | Malmin | 433/224 |
| 3,964,170 | 6/1976 | Zdarsky | 433/72 |
| 4,044,468 | 8/1977 | Kahn | 433/102 |
| 4,299,571 | 11/1981 | McSpadden | 433/122 |
| 4,332,561 | 6/1982 | McSpadden | 433/102 |
| 4,518,356 | 5/1985 | Green | 433/102 |
| 4,536,159 | 8/1985 | Roane | 433/224 |

FOREIGN PATENT DOCUMENTS 0464121  7/1928  Fed. Rep. of Germany ...... 433/102

OTHER PUBLICATIONS

"The Effect of Preparation Procedures on Original Canal Shape and on Apical Foramen Shape", by Franklin S. Weine et al., Journal of Endodontics, vol. 1, No. 8, Aug. 1985, pp. 225–262.

Primary Examiner—John J. Wilson
Assistant Examiner—Adriene J. Lepiane
Attorney, Agent, or Firm—Henry M. Bissell

[57] ABSTRACT

A series of instruments for use in cleaning and shaping the root canal of a tooth is disclosed. The instruments are files having increasing tapers on sequentially-used files, with all of the files having the same, or nearly the same, small diameter at the tip of the cutting surface. The files create an increasingly tapered aperture in the root canal, which is exactly sized to admit a selected one of a set of variable taper filling materials available for filling a prepared root canal. Each file also has a safe edge to eliminate perforating the root canal, a rounded tip to eliminate ledging, and a handle shaped to provide a tactile reference to the orientation of the safe edge.

22 Claims, 2 Drawing Sheets

ANTI-CURVATURE DENTAL ROOT CANAL SHAPING FILE

BACKGROUND OF THE INVENTION

1. Field of the Invention

The present invention relates generally to endodontic instruments and, more particularly, to root canal files or reamers used in the cleaning of material present in the root canal of a human tooth and for enlarging and shaping the root canal so that it may be prepared for filling.

2. Description of the Prior Art

A relatively common but difficult dental procedure is the cleaning and filling of the root canal of a patient's tooth. In the performance of a root canal procedure, a hole is first cut in the crown or exposed portion of the tooth, typically ether in the biting surface of the tooth, for posterior teeth or in the side of the tooth on the interior of the jaw for incisor teeth. Small endodontic instruments known generally as root canal files are then used to clean out the material present in the root canal, and to shape the root canal so that a tapered filling material may be inserted into the root canal to fill it. An example of such an instrument, also called a broach, is shown in U.S. Pat. No. 250,544.

Two types of instruments are in general use as root canal files, namely the Hedstrom instrument and the K-type instrument. The K-type instrument is an axially twisted, tapered, triangular or square cross-sectional shaft which has three or four spiral cutting edges along the tapered shaft and a conical tapered tip on the end thereof. The Hedstrom-type instrument is a lathe-cut file having a round tapered shaft with one or two spiral cutting flutes machined into the shaft all the way to the tip. The main difference resulting from the construction of the two types of files is that the K-type file will cut in either rotational direction, or when moved up and down, while the Hedstrom-type file will cut only when moved up and down in the root canal.

When a root canal is being cleaned and shaped, a series of files having increasing diameters is used to gradually enlarge the root canal. The files are held between the thumb and forefinger of one hand by the dentist. Each file in a set of the known prior art has an identical taper from one end to the other. For example, in a typical K-type file set the taper is 0.32 millimeters on ever file, with the files coming in a number of sizes. The size number charcterizing the file is the diameter of the file at the tip in hundredths of a millimeter, and the diameter of th file at the large end is thus 0.32 millimeters greater than this tip diameter. A complete set will include sizes 06, 08, 10, 15, 20, 25, 30, 35, 40, 45, 50, 55, 60, 70, 80, 90, 100, 110, and 120, while sizes 8-60 will typically be used. Hedstrom-type instruments similarly come in sets of increasing size, typically from 0.10 to 1.40 millimeter tip size, with 0.15-0.60 millimeter tip sizes typically being used.

Unlike the files, root canals are seldom straight. If the files which are used deviate substantially from the original curvature of the root canal, the tooth may be irreversibly damaged. If the file is too straight and cuts through the side of the root, which is referred to as a perforation of the root, the tooth must then be removed. If the tip of the file does not follow the curvature of the canal and bores a passage branching out from the root canal, which is referred to as ledging, surgical correction of the problem is necessitated.

It is therefore apparent that the files must be bent prior to insertion into the root canal and use of the files to prepare the root canal. Such bending of the files is preferably done by the instrument described in my U.S. patent application Ser. No. 899,342, entitled "Endodontic Root Canal File Bending Pliers", and filed concurrently with the present application, and that application is hereby incorporated herein by reference. While the files having smaller diameters may be easily bent, the larger diameter files do not bend easily.

In addition to bending the file, it is necessary to pull a precurved file along the outside of the canal curvature when shaping the canal to avoid perforating the root. This technique is called an anti-curvature motion, is difficult to teach to dentists, and is time-consuming for even the most skilled practitioners to perform.

It is thus apparent that the art of root canal filing is one which requires great skill to prevent damage to the tooth. The technique used with a set of files having an identical taper to clean and shape the root canal is referred to as the "step-back" technique, with each successively larger file being used further back from the end of the canal. This technique is, at best, a difficult and time-consuming method.

A slightly different file is disclosed in U.S. Pat. No. 4,536,159, to Roane. The Roane file rounds the cutting edges near the tip of the file, in an attempt to prevent the file from ledging the root canal. While the Roane file may reduce or eliminate occurrences of ledging, it will not do anything about the more serious problem of perforating the curved roots of teeth.

Other types of files have been developed for similar purposes. The U.S. Pat. No. 4,260,379 of Graves et al discloses a file of rhomboidal cross section in which a tapered blade is ground to develop an oblique parallelogram and twisted. McSpadden U.S. Pat. No. 4,299,571 discloses a file with a blunt tip with approximately 3 mm of non-cutting file provided adjacent the end. U.S. Pat. No. 4,332,561, also of McSpadden, combines the pilot tip of the earlier McSpadden patent with double-fluted design to develop a Hedstrom-type file.

It is therefore apparent that it would be desirable to have a file design which could eliminate or reduce the instances of both ledging and perforation. Achieving these objectives is the main object of the present invention. In addition, it is an object of the present invention to minimize the time and effort necessary to clean and shape the root canal. Finally, the present invention also seeks to reduce the level of training and skill necessary to properly perform root canal operations.

SUMMARY OF THE INVENTION

The disadvantages and limitations of the background art discussed above are overcome by the present invention. The present invention differs significantly and advantageously from the files discussed above in two respects. First, rather than using a series of files of differing sizes but the same taper, the present invention uses a series of files with different tapers. Secondly, one side of the files does not have a cutting surface thereon.

With regard to the first feature of the present invention, several advantages over the art are achieved by using files with different tapers. The purpose of endodontic shaping procedures is to create a continuously tapering preparation which is narrowest at the end of the canal, and widest near the crown of the tooth. Rather than doing this by the difficult and time-consuming step-back technique, the present invention uses progressively greater tapers on a succession of files to effectively and efficiently clean and shape the root canal.

By using a series of files with differing tapers, it has been determined that the root canal may be prepared by using only three or four files instead of the nine or ten files required by conventional files. While it is readily apparent that the use of only three or four tools instead of nine or ten tools is desirable from a standpoint of efficiency, it should be noted that the result is at least as good as that obtained by conventional files, and in most cases the result is better.

Since the design of files taught by the present invention uses different tapers, the tip of the file is not used to cut as in files with a standard taper. Whereas standard file sets have increasing tip diameters in the sequence of files, the tip diameters of files constructed according to the present invention are all identical or nearly identical. Under the present invention, the differeence in file size occurs along the files in increasing amounts from the tip to the end nearest the handle, and it is at the end nearest the handle that the largest variation in diameter between files occurs.

Since the tip size remains constant under the present invention, and since the tip is not used for cutting to the extent in previous file designs, the tip may be rounded, thus preventing ledging of the root canal. This benefit is obtained as in incidental advantage to the varying of tapers between files.

The second important difference between the present invention and the art is that files constructed according to the teachings of the present invention have a "safe edge" on the cutting flutes. This safe edge is along one side of the file, and will not cut when the file is used. By properly positioning the file, the safe edge will be facing the inside curvature of the root canal, and will not cut through the side of the root even if the file is not properly bent. It may thus be perceived that the problem of perforating the root is also eliminated by the files of the present invention.

In addition, since the anti-curvatuve motion is no longer necessary, the time as well as the skill needed to perform the root canal procedure is greatly reduced. The present invention thus represents a great improvement in the dental arts, in that the procedure is simpler, easier, and requires fewer tools. In addition, the potential negative effects of the performance of a root canal, namely perforating the root or ledging the canal passage, are essentially eliminated. The present invention achieves these advantages with no relative disadvantages.

BRIEF DESCRIPTION OF THE DRAWING

A better understanding of the present invention may be had from a consideration of the following detailed description, taken in conjunction with the accompanying drawing in which.

DETAILED DESCRIPTION OF THE PREFERRED EMBODIMENT

Figure 1:
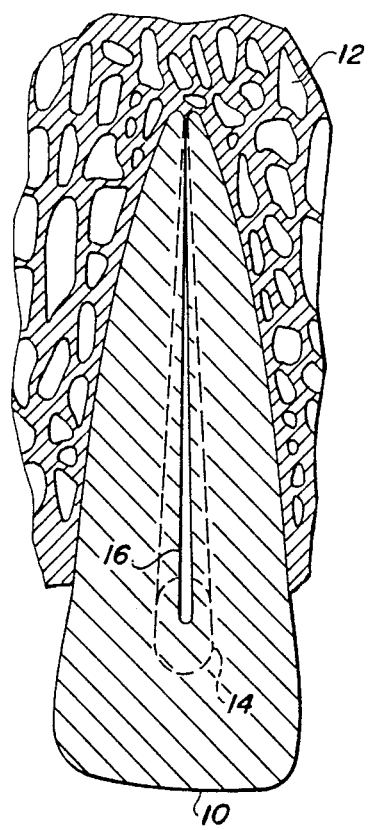
FIG. 1 is a somewhat schematic view of a root canal in a tooth, with the portion to be removed shown in dotted lines.
Figure 3:
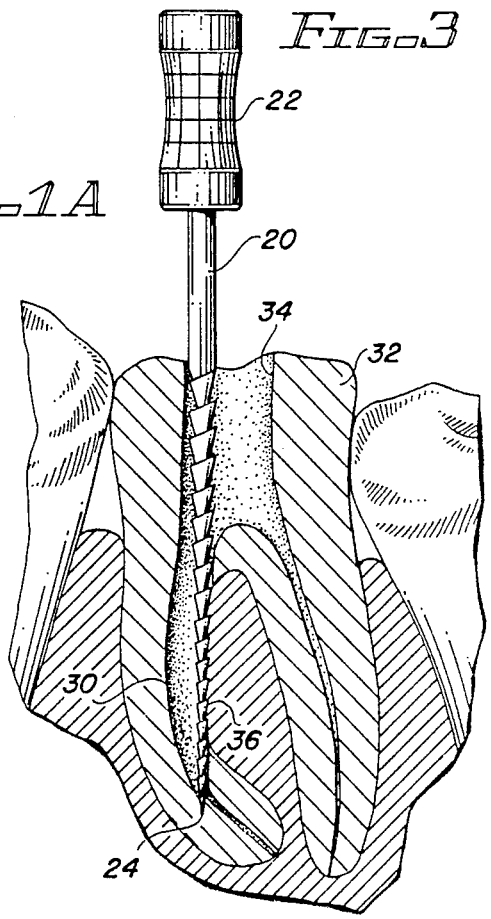
FIG. 3 is a schematic view of the conventional file of FIG. 1A being used to clean and shape the root canal, and specifically illustrates both perforating and ledging of the root canal.
Figure 2:
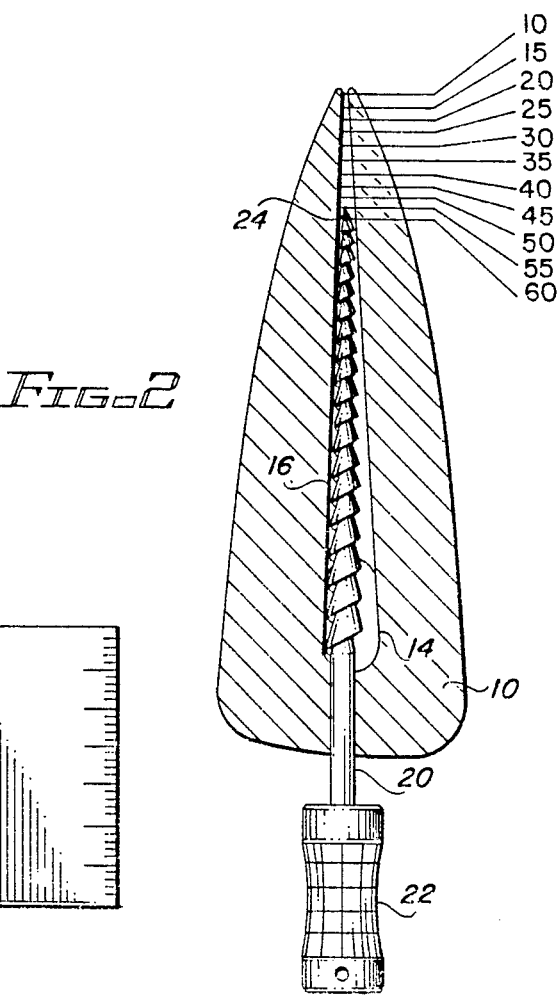
FIG. 2 shows the final intrusion of the tips of each of eleven conventional files into the root canal of FIG. 1, thereby illustrating the step-back technique.

Before discussing the present invention, it is helpful to discuss briefly the root canal procedure as shown in FIGS. 1-3. FIG. 1 shows a tooth 10 located in the bone 12 of a jaw. The tooth 10 in FIG. 1 is an incisor, and the opening in the crown of the tooth 10 is cut on the side of the tooth 10 in the interior side of the jaw (not shown), which opening is generally indicated at 14. The tooth 10 has a root canal 16 therein, extending from the interior of the crown of the tooth 10 to the tip of the tooth 10 which is embedded in the bone 12.

Figure 1A:
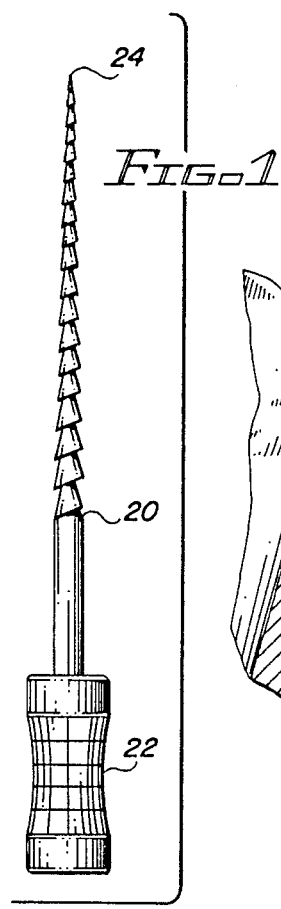
FIG. 1A shows a conventional Hedstrom-type file.

Also shown in FIG. 1A is a Hedstrom-type file 20, having a handle 22 supporting the file 20. The file 20 has a sharp tip 24, which is needed since each successive file in a series has a larger diameter at the tip. It should be noted that while the discussion of the prior art uses as an example a Hedstrom-type file, it is equally applicable to other configurations of like-tapered root canal file designs. Similarly, as will become evident later, the description of the preferred embodiment will discuss modifications to a Hedstrom-type file, and this discussion will also not be a limitation of the present invention to use with a Hedstrom-type design.

Referring now to FIG. 2, the file 20 is shown inserted into the root canal 16, which is enlarged from the view shown in FIG. 1. With conventional files, the step-back technique discussed above is used, with each progressively larger file being inserted shallower and shallower into the root canal 16. The numbers along the root canal 16 near the tip end of the root canal 16 represent the maximum extent to which different size files are inserted, with file sizes from 10 to 60 (representing tip diameters from 0.10 to 0.60 millimeters) being used. As mentioned above, between nine and eleven files are required, with more occasionally being necessary.

Referring next to FIG. 3, the file 20 is shown inserted into a root canal 30 in a molar tooth 32. As apparent, for the molar tooth 32 a hole 34 to admit the file 20 is present in the biting surface of the tooth 32. Since the file 20 was not curved enough, it has perforated the curved root canal 30 at the location indicated by the reference numeral 36. As mentioned above, perforation can also occur when the file 20 is not pulled against the outside curve of the root canal 30 by using the anti-curvature motion discussed above.

Another problem shown in FIG. 3 is that the tip 24 of the file 20 has left the root canal 30 and cut a ledge along the outside curvature of the root canal 30. Succeeding files may well become trapped in the ledge also, and will not properly clean and shape the root canal 30. The present invention eliminates both perforation and ledging of a root canal, and in addition makes the root canal operation quicker and easier to perform.

Figure 4:
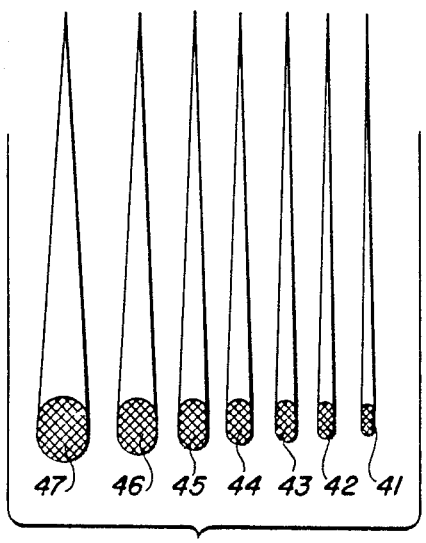
FIG. 4 shows the seven sizes of variable taper filling material which are commercially available for selection in filling a prepared root canal.

There are, as mentioned previously, seven varying tapers for root canal filling materials available from one particular vendor. These are shown in FIG. 4. The variable taper filling materials 41, 42, 43, 44, 45, 46, and 47 vary in size with 41 being the smallest and 47 being the largest.

Figure 5:
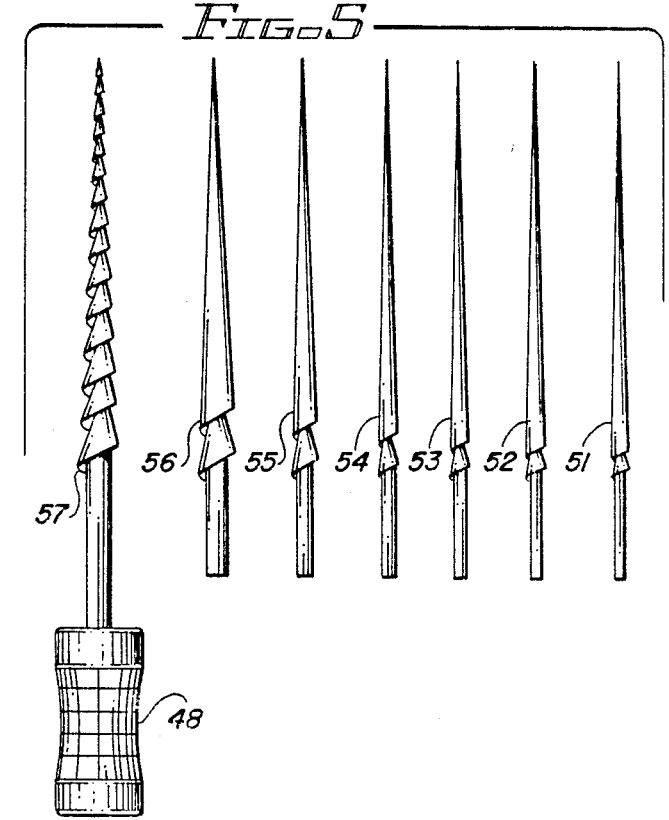
FIG. 5 illustrates the seven sizes of files of comparable dimension, constructed according to the teachings of the present invention, with the handles removed for purposes of the illustration from six of the files.

The preferred embodiment uses a series of seven files 51, 52, 53, 54, 55, 56, and 57, which are shown in FIG. 5. Typically, only three or four files will be used in cleaning and shaping the root canal, a vast improvement over the art. Although only file 57 is shown with a handle 48, all of the files have handles, of course. The files 51, 52, 53, 54, 55, 56, and 57 all have the same small diameter at the tips, with different diameters at the ends opposite the tips, and hence different tapers.

This is a crucial departure from the art, the result of which, with the other modifications described below, makes the root canal procedure much quicker and easier to perform. Since the tip diameter of each file 51, 52, 53, 54, 55, 56, and 57 is identical or nearly identical, each file will be inserted all the way, unlike the previously known files discussed above in conjunction with FIG. 2. The sizes of the files 51, 52, 53, 54, 55, 56 and 57 correlate exactly to the sizes of the corresponding tapered filling materials 41, 42, 43, 44, 45, 46, and 47.

Figures 6A, 6B:
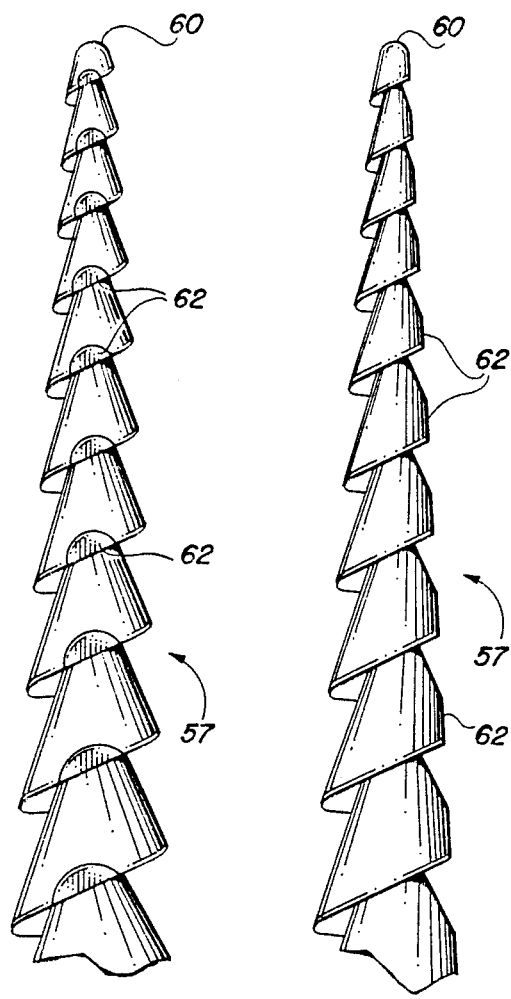
FIG. 6A illustrates the cutting portion of one of the files of FIG. 5, specifically showing the rounded tip, and also the safe edge in plan view.
FIG. 6B illustrates the cutting portion of one of the files of FIG. 5, specifically showing the rounded tip, and also the safe edge in side view.

Referring next to FIGS. 6A and 6B, the other two features constituting improvements over the prior art are apparent. The file 57, like the other files 51, 52, 53, 54, 55 and 56, which are not shown in detail, has a rounded tip 60, which will effectively and completely prevent ledging. The rounded tip 60 is possible since all of the files 51, 52, 53, 54, 55, 56, nd 57 have the same or nearly the same small tip diameter. This small tip diameter is small enough to allow entry of each file all the way into the root canal.

Another feature of the preferred embodiment is also shown in FIGS. 6A and 6B. On one side of the file 57 there is a safe edge, which constitutes a number of flat surfaces 62 on the otherwise sharp cutting edges on that side of the file 57. The flat surfaces 62 may be machined or polished onto the side of the file 57. Likewise, the files 51, 52, 53, 54, 55, and 56 all have safe edges.

Figures 7A, 7B:
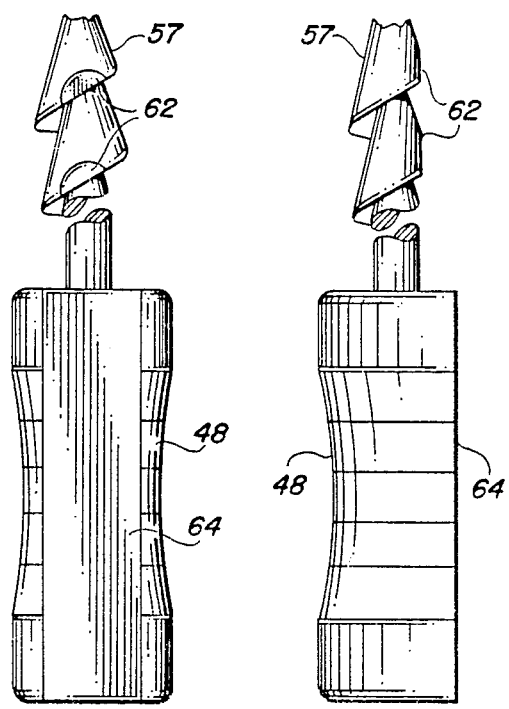
FIG. 7A shows the flat surface of the handle of one of the files of FIG. 5, which is used to orient the safe edge of the file, in plan view.
FIG. 7B shows the flat surface of the handle of one of the files of FIG. 5, which is used to orient the safe edge of the file, in side view.

By orienting the safe edge toward the inside curve of the root canal when a file is in the root canal, perforating the root canal is prevented. This obviates the need to use the anti-curvature motion discussed above, and thereby minimizes both the time and level of skill needed to clean and shape the root canal. The file 57 may be positioned by providing a flat surface 64 on the handle 48, which flat surfacce 64 is oriented with the flat surfaces 62 on the file 57, as shown in FIGS. 7A and 7B.

Figure 8:
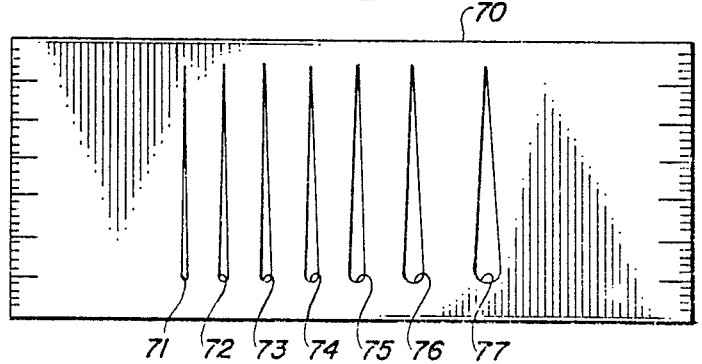
FIG. 8 shows a precision template for measuring taper size for selecting a file or a filling.

FIG. 8 shows a precision template 70, having seven areas 71, 72, 73, 74, 75, 76, and 77 which are sized to exactly admit the seven variable taper filling materials 41, 42, 43, 44, 45, 46, and 47. The template 70 may be used to select the size file to be used by superimposing the template 70 on an X-ray of the tooth.

It may now be appreciated that the present invention possesses a number of advantages over the art. Both ledging and perforating of the root canal are prevented. Only three of four files of the present invention are needed to perform a root canal operation, compared with nine or eleven for other files. The root canal operation is easier, safer, and more efficient to perform when using the files of the present invention. Finally, since the files of the present invention gradually expand the taper created in the root canal (instead of creating the tapered enlarged root canal area in nine or ten segments virtually guaranteed to be anything but smooth), the taper created in the root canal is perfectly smooth, and will exactly fit the selected tapered filling material corresponding to the last file used. The present invention brings with it no attendant disadvantages, and therefore represents a highly desirable improvement in the art.

Although there have been described above specific arrangements of an anti-curvature dental root canal shaping file in accordance with the invention for the purpose of illustrating the manner in which the invention may be used to advantage, it will be appreciated that the invention is not limited thereto. Accordingly, any and all modifications, variations or equivalent arrangements which may occur to those skilled in the art should be considered to be within the scope of the invention as defined in the annexed claims.

What is claimed is:

1. An endodontic instrument for cleaning and shaping a root canal in a tooth, comprising:
    a first file having thereon a tapered portion, said tapered portion having a larger diameter at one end thereof and a smaller diameter at the other end thereof, said first file having a tip at the end of said tapered position having said smaller diameter;
    cutting edges disposed on said tapered portion about the circumference thereof, with the cutting edges being altered to prevent cutting along substantially the entire extent of one longitudinal side of said tapered portion; and
    a rounded surface disposed at said tip of said first file.

2. An endodontic instrument as defined in claim 1 comprising a plurality of files, each having a tapered portion with cutting edges disposed thereon about the circumference and the cutting edges being altered to prevent cutting along substantially the entire extent of one longitudinal side of the tapered portion, each file of said plurality having a different taper from the others, said files increasing in taper from the first to the last of said plurality.

3. An endodontic instrument as defined in claim 2 wherein the taper of said tapered portion of each file corresponds respectively to the taper of a series of variable taper filling materials available to fill a prepared root canal.

4. An endodontic instrument as defined in claim 3 further comprising in combination therewith:
    a template having a plurality of shapes therein corresponding to the sizes of variable taper filling materials, said template being for use as a reference in selecting the size of the taper of the corresponding file.

5. An endodonitc instrument as defined in claim 3 wherein the files having the smaller taper are for use prior to use of the files having a larger taper.

6. An endodontic instrument as defined in claim 1 additionally comprising:
    a handle mounted on said file at the end of said tapered portion having the larger diamter, said handle having a tactile identifying element thereon, which identifying element is oriented relative to said longitudinal side of said tapered portion with said cutting edges being altered.

7. An endodontic instrument as defined in claim 6 wherein said handle is essentially round in cross-section, and said identifying element comprises a flat side on said handle.

8. A file for cleaning and shaping a root canal in a tooth, comprising:
   a tapered shaft having a smaller diameter at one end thereof and a larger diameter at the other end thereof;
   a plurality of cutting surfaces located in said tapered shaft from said larger diameter end nearly to said smaller diameter end;
   a safe edge on said file resulting from the drilling of said cutting surfaces along one entire longitudinal side of said tapered shaft; and
   a rounded surface machined onto a tip of said shaft at the end of said shaft having said smaller diameter.

9. A plurality of files as defined in claim 8, each file having a different degree of taper from the others, the degree of taper of the files corresponding respectively to the sizes of variable taper filling materials available for filling root canals.

10. A series of files for use in succession in cleaning and shaping a root chanal in a tooth, comprising:
    a first shaft having a first taper, said first shaft having a smaller diameter at one end thereof and a larger diameter at the other end thereof, said first shaft having cutting surfaces located therein from said larger diameter end nearly to said smaller diameter end, said cutting surfaces having been removed from one longitudinal side of said first shaft, said first shaft having a rounded tip at the end of said first shaft having said smaller diameter; and
    a second shaft having a second taper, said second taper being greater than said first taper, said second shaft having a smaller diameter at one end thereof and a larger diameter at the other end thereof, said second shaft having cutting surfaces located therein from said larger diameter end nearly to said smaller diameter end, said cutting surfaces having been removed from one longitudinal side of said second shaft, said second shaft having a rounded tip at the end of said second shaft having said smaller diameter.

11. A series of files as defined in claim 10 wherein the one of said first and second shafts having the smaller taper is used before the other of said first and second shafts.

12. A set of instruments for cleaning and shaping a root canal of a tooth, comprising:
    a plurality of files, each including a shaft having a different taper from the others, said files all having cutting surfaces located in their shafts, said cutting surfaces having been dulled along one longitudinal side of each of said files, said files having a rounded tip at the smaller end of their shafts, the files being for use in succession from the smaller tapers to the larger tapers.

13. An endodontic file for cleaning and shaping a root canal, comprising:
    a tapered shaft which is axially twisted, said tapered shaft having a plurality of spiral cutting surfaces along the length thereof and a conical tapered tip on the smaller end thereof, said tapered tip having a rounded end to prevent ledging, said cutting surfaces being dulled along one full side of said tapered shaft, thereby producing a safe edge.

14. A file as defined in claim 13 further including a handle mounted on said file, the handle having tactile reference means for locating the alignment of said safe edge.

15. A file as defined in claim 14 wherein the tactile reference means comprise a flat side on a generally round handle, the flat side being oriented in alignment with said safe edge.

16. An endodontic file for cleaning and shaping a root canal, comprising:
    a round tapered shaft having cutting surfaces machined into said shaft along the length of said shaft all the way nearly to the smaller end of said shaft, a portion of said cutting surfaces being absent along one full side of said shaft; and
    a rounded tip at said smaller end of said shaft.

17. A method of making a file for cleaning and shaping a root canal in a tooth, comprising:
    (a) providing a tapered shaft having a smaller diameter at one end thereof and a larger diameter at the other end thereof;
    (b) forming cutting surfaces in said tapered shaft from said larger end nearly to said smaller end;
    (c) removing said cutting surfaces from the full extent of one longitudinal side of said tapered shaft to develop a safe edge which is free of cutting surfaces; and
    (d) machining a rounded surface onto a tip of said shaft at the end having said smaller diameter.

18. The method of claim 17 comprising:
    providing a plurality of tapered shafts for making a plurality of said files, each of said shafts having a different degree of taper from the next; and
    for each individual file forming cutting surface in said tapered shaft from said larger end nearly to said smaller end; removing said cutting surfaces from the full extent of one longitudinal side of said tapered shaft to develop a safe edge which is free of cutting surfaces; and machining a rounded surface onto a tip of said shaft at the end having said smaller diameter.

19. The method of claim 18 further comprising selecting the degree of taper of each shaft to be substantially equal to a corresponding one of a set of variable taper filling materials availble for filling prepared root canals.

20. An endodontic instrument for cleaning and shaping a root canal in a tooth, comprising:
    a first file having thereon a tapered portion, said tapered portion having a larger diameter at one end thereof and a smaller diameter at the other end thereof, said first file having a tip at the end of said tapered portion having said smaller diameter;
    cutting edges disposed on said tapered portion about the circumference thereof except along substantially the entire extent of one longitudinal side of said tapered portion; and
    a rounded surface disposed at said tip of said first file.

21. An endodontic instrument as defined in claim 20 comprising a plurality of files, each having a tapered portion with cutting edges disposed thereon about the circumferences except along substantially the entire extent of one longitudinal side of the tapered portion, each file of said plurality having a different taper from the others, said files increasing in taper from the first to the last of said plurality.

22. A set of instruments for cleaning and shaping a root canal of a tooth, comprising:
a plurality of endodontic files, each including a shaft having a different taper from the others, each of said files having cutting surfaces located about the major circumferential extent of its shaft except along one longitudinal side thereof, said files having a rounded tip at the smaller end of their shafts, the files being for use in succession from the smaller taper files to be larger taper files.

* * * * *